US00PP20744P2

(12) United States Plant Patent
Zary

(10) Patent No.: US PP20,744 P2
(45) Date of Patent: Feb. 9, 2010

(54) FLORIBUNDA ROSE PLANT NAMED 'JACPERBY'

(50) Latin Name: *Rosa hybrida*
Varietal Denomination: JACperby

(75) Inventor: Keith W. Zary, Thousand Oaks, CA (US)

(73) Assignee: Jackson & Perkins Wholesale, Inc, Hodges, SC (US)

( * ) Notice: Subject to any disclaimer, the term of this patent is extended or adjusted under 35 U.S.C. 154(b) by 0 days.

(21) Appl. No.: 12/290,005

(22) Filed: Oct. 24, 2008

(51) Int. Cl.
*A01H 5/00* (2006.01)

(52) U.S. Cl. ..... Plt./141

(58) Field of Classification Search ..... Plt./141
See application file for complete search history.

*Primary Examiner*—Susan B McCormick Ewoldt
(74) *Attorney, Agent, or Firm*—Klarquist Sparkman, LLP

(57) ABSTRACT

A new and distinct variety of floribunda rose plant, substantially as herein shown and described, characterized particularly by its compact rounded growth habit; large clusters of lavender flowers having a strong citrus fragrance; glossy dark green foliage; and resistance to rust and powdery mildew.

1 Drawing Sheet

Genus and species: *Rosa hybrida.*
Variety denomination: 'JACperby'.

Origin of the Invention

The present invention relates to a new and distinct variety of a Floribunda rose plant named 'JACperby' which was originated by me by crossing the variety JACshok, U.S. Plant Pat. No. 11,562 (the seed parent), with the variety 'Blue Bajou', not patented (the pollen parent).

BACKGROUND OF THE INVENTION

The primary objective of this breeding was to produce a new floribunda rose variety having the following characteristics: a strong fragrance, lavender flower color, flowers in large clusters, compact rounded plant habit and dark green glossy foliage.

BRIEF SUMMARY OF THE INVENTION

The objective was substantially achieved, along with other desirable improvements, as evidenced by the following unique combination of characteristics, that are outstanding in the new variety, and that distinguish it from its parents, as well as from all other varieties of which I am aware:

1. Strong citrus fragrance.
2. Large clusters of nine to eleven flowers.
3. Compact rounded growth habit.
4. Dark green glossy foliage.
5. Attractive lavender flower color.

Asexual reproduction of this new variety by cuttings, as performed at Wasco, Calif., shows that the foregoing and all other characteristics and distinctions come true to form and are established and transmitted through succeeding propagations.

Comparison with Parents

The female parent 'JACshok' has flowers with 25 to 30 petals, and clusters of three to seven flowers, while 'JACperby' has flowers with 20 to 25 petals and clusters of nine to eleven flowers. The male parent 'Blue Bajou' is very susceptible to powdery mildew, while 'JACperby' is resistant to powdery mildew.

Comparison with Similar Variety

'JACshok', compared above, is believed to be the most similar variety.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart © 2001, except where ordinary dictionary significance of color is indicated. The observations are of plants that were about 4 years of age (observed from January 2007 to October 2008) and that were grown in a garden environment at Somis, Calif.

PARENTAGE

*Seed parent.*—'JACshok' (U.S. Plant Pat. No. 11,562).
*Pollen parent.*—'Blue Bajou' (not patented).

Flower:

*Blooming Habit.*—Recurrent.

Bud:

*Size.*—About 25 mm long and 20 mm in diameter when the petals start to unfurl.

*Form.*—The bud form is long and pointed ovoid.

*Color.*—When sepals first divide, bud color is Purple Group 76B. When half blown, the upper sides of the petals are, Purple Group N78B in the center of the flower and Purple Group N78C on the edges; and the lower sides of the petals are Purple Group 76B.

*Sepals.*—Color: Upper surface: Green Group 138B overlain in bright sun with Greyed-Purple Group 186B. Lower surface: Yellow-Green Group 146C. Length: 20 to 25 mm. Width: 5 mm. Shape: Subulate. Surface texture: Hoary. There are three lightly appendaged sepals. There are two unappendaged sepals with hairy edges.

*Receptacle.*—Color: Yellow-Green Group 147B. Shape: Funnel. Size: Medium, about 12 mm long×9 mm wide. Surface: Smooth.

*Peduncle.*—Length: Medium, averaging about 50 mm. Surface: Smooth. Color: Yellow-Green Group 146D. Strength: Stiff, erect.

Bloom:

*Size.*—Medium. Average open diameter is about 8 to 9 cm.

*Borne.*—Several together in clusters of 9 to 11 blooms having a flat shape.

*Stems.*—Strength: Strong. Average length is about 30 to 35 cm with a diameter of 8 to 9 mm.

*Form.*—When first open: Bloom is high centered. Permanence: Retains its form to the end; outer petal edges curl slightly.

*Petalage.*—Number of petals under normal conditions: 20 to 25.

*Color.*—The upper sides of the petals are Purple Group N78B in the center of the flower and Purple Group N78C on the edges of the flower. The reverse sides of the petals are Purple Group 76B. The base of each petal has 5 mm×5 mm Yellow Group 4D color spot. The major color on the upper side is Purple Group N78B.

*Variegations.*—None.

*Discoloration.*—The general tonality at the end of the first day: No change. At the end of the third day: Some fading on outer petals to Purple Group N78C.

*Fragrance.*—Strong with a citrus character.

Petals:

*Thickness.*—Thin.

*Shape.*—Round.

*Surface.*—Smooth.

*Margin.*—Entire. Apex Shape: Cuspidate. Base Shape: Rounded.

*Form.*—Flat with tips slightly recurved.

*Arrangement.*—Imbricated.

*Petaloids.*—Number: 3 to 5, 7 to 20 mm long×3 to 8 mm wide. Color: upper: Purple Group N78B in the centre of the flower and Purple Group N78C on the edges of the flower. lower: Purple Group 76B.

*Persistence.*—Petals drop off cleanly before drying.

*Lastingness.*—On the plant: Long (about 5 to 7 days). As a cut flower: Long (about 7 to 9 days).

Reproductive parts:

*Stamens.*—Number: 100 to 120. Length: 8 to 12 mm. Anthers: Length: 1 mm. Color: Greyed-Orange Group 168D. Arrangement: Regular around styles. Filaments: Color: Greyed-Yellow Group 161D. Length: 7 to 11 mm. Pollen: Color: Greyed-Orange Group 171 C.

*Pistils.*—Number: 60 to 80. Length: 5 to 7 mm. Styles: Color: Red Group 46D. Length: 4 to 6 mm. Stigmas: Color: Greyed-Orange Group 165C. Length: 1 mm.

*Hips.*—Color: Yellow-Green Group 147B. Shape: Round. Size: 18 to 20 mm diameter.

PLANT

*Form.*—Bush.

*Growth.*—Vigorous; branching.

*Age to maturity.*—2 years.

*Mature plant.*—Height: About 80 to 100 cm. Width: About 80 to 90 cm.

*Rootstock.*—Own root.

Foliage: Number of leaflets on normal mid-stem leaves: 5 to 7.

*Size.*—Medium, about 8 to 12 cm long×6 to 8 cm wide.

*Quantity.*—Normal.

*Color.*—New foliage: Upper side: Greyed-Red Group 178A Lower side: Greyed-Red Group 178A. Old foliage: Upper side: Green Group 139A. Lower side: Green Group 139C.

Leaflets:

*Size.*—About 3.5 to 4 cm long×2.5 to 3 cm wide.

*Shape.*—Broadly oval.

*Base shape.*—Rounded.

*Apex shape.*—Acuminate.

*Texture.*—Leathery.

*Edge.*—Serrated.

*Serrations.*—Single.

*Petiole.*—Color: Yellow-Green Group 147B.

*Petiole rachis.*—Color: Yellow-Green Group 147B. Underside: Prickles.

*Stipules.*—Length: 15 mm.

*Disease resistance.*—Susceptible to blackspot; mildew and rust resistant under normal growing conditions.

*Pest resistance.*—Not observed.

*Vein color.*—Yellow-Green Group 147B.

*Venation pattern.*—Reticulate.

Wood:

*New wood.*—Color: Yellow-Green Group 148A and Greyed-Red Group 180A. Bark: Smooth.

*Old wood.*—Color: Yellow-Green Group 146B. Bark: Smooth.

Prickles:

*Quantity.*—On main canes from base: None. On laterals from main canes: Few (6 to 8 per 20 cm).

*Form.*—Straight.

*Length.*—8 to 10 mm.

*Color when young.*—Greyed-Red Group 178C.

*Color when mature.*—Greyed-Orange Group 164C.

Small prickles:

*Quantity.*—On main stalks: None. On laterals: None.

Winter hardiness: Hardy to Zone 5.

I claim:

1. A new and distinct variety of floribunda rose plant, substantially as herein shown and described, characterized particularly by its compact rounded growth habit; large clusters of lavender flowers having a strong citrus fragrance; glossy dark green foliage; and resistance to rust and powdery mildew.

* * * * *

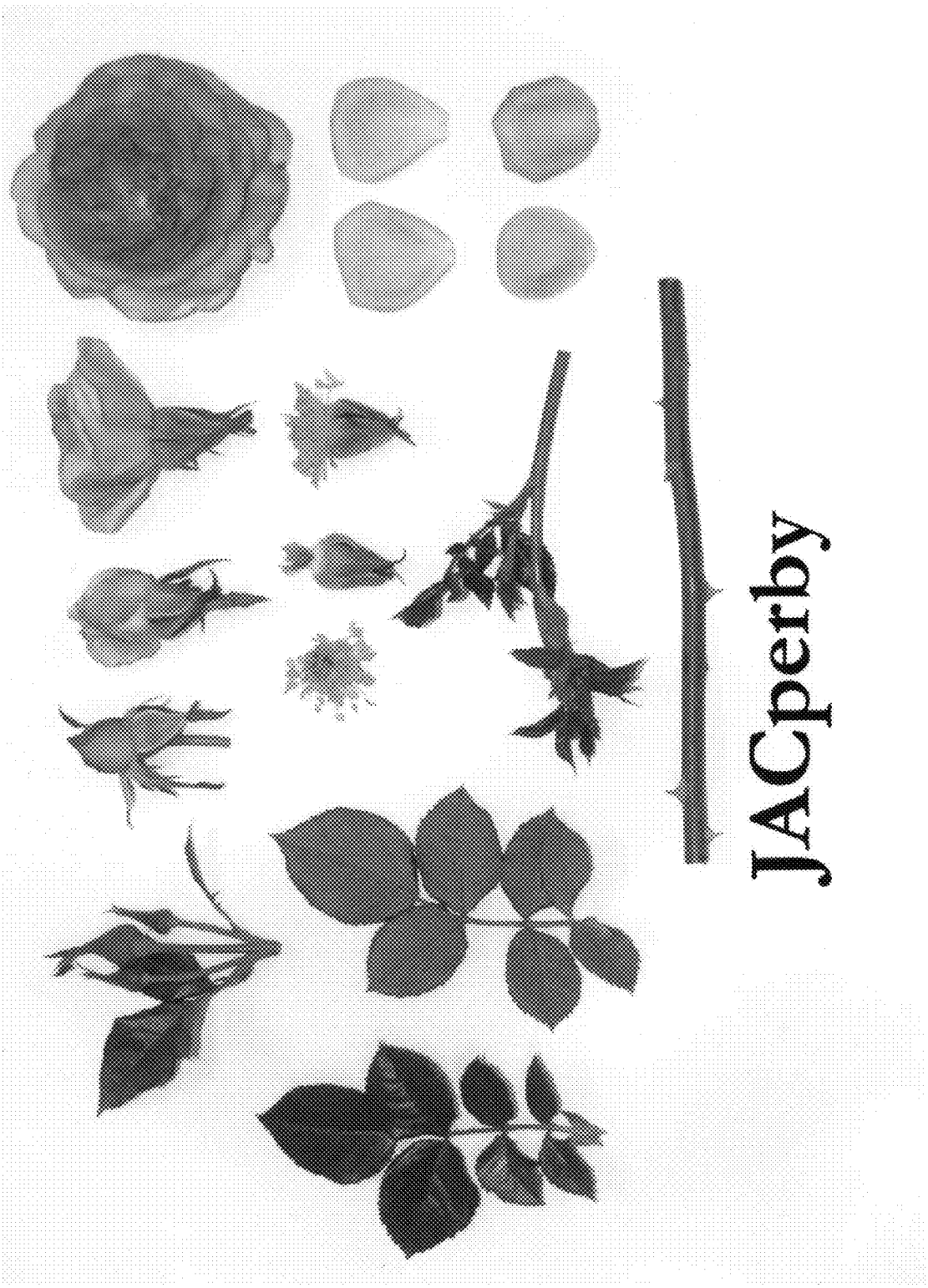
JACperby